(12) United States Patent
Kim et al.

(10) Patent No.: US 9,896,710 B2
(45) Date of Patent: Feb. 20, 2018

(54) GLYCOSYLTRANSFERASE DERIVED FROM DOLWOE AND USE THEREOF

(71) Applicants: KOREA ADVANCED INSTITUTE OF SCIENCE AND TECHNOLOGY, Daejeon (KR); INTELLIGENT SYNTHETIC BIOLOGY CENTER, Daejeon (KR)

(72) Inventors: Sun-Chang Kim, Dejeon (KR); Giltsu Choi, Dejeon (KR); Suk-Chae Jung, Daejeon (KR); Woohyun Kim, Daejeon (KR); Soohwan Lim, Daejeon (KR); Wan-Taek Im, Daejeon (KR)

(73) Assignees: Korea Advanced Institute of Science and Technology, Daejeon (KR); Intelligent Synthetic Biology Center, Daejeon (KR)

( * ) Notice: Subject to any disclaimer, the term of this patent is extended or adjusted under 35 U.S.C. 154(b) by 65 days.

(21) Appl. No.: 14/857,703

(22) Filed: Sep. 17, 2015

(65) Prior Publication Data

US 2016/0083767 A1    Mar. 24, 2016

(30) Foreign Application Priority Data

Sep. 19, 2014 (KR) .................. 10-2014-0125149

(51) Int. Cl.
| | |
|---|---|
| *C12P 19/18* | (2006.01) |
| *C12N 9/10* | (2006.01) |
| *C12N 1/00* | (2006.01) |
| *C12P 33/20* | (2006.01) |
| *C12P 19/56* | (2006.01) |

(52) U.S. Cl.
CPC ............ *C12P 33/20* (2013.01); *C12N 9/1051* (2013.01); *C12P 19/56* (2013.01); *C12Y 204/01* (2013.01)

(58) Field of Classification Search
None
See application file for complete search history.

(56) References Cited

FOREIGN PATENT DOCUMENTS

| KR | 2014-0041259 A | 4/2014 |
|---|---|---|
| KR | 2014-0041261 A | 4/2014 |

OTHER PUBLICATIONS

Yue et al., Biotechnol. Bioeng. 89:444-452, 2005.*
Kim et al., Biotechnol. Adv. 33:717-735, 2015.*
GenBank Database Accession No. AED99883, Mar. 2012, 1 page.*
Ajikumar et al., "Isoprenoid Pathway Optimization for Taxol Precursor Overproduction in *Escherichia coli*," Science, (2010), 330(6000), pp. 70-74.
Oh, et al., "PIL5, Phytochrome-Interacting Basic Helix-Loop-Helix Protein, Is a Key Negative Regulator of Seed Germination in *Arabidopsis thaliana*," Plant Cell, vol. 16, (2004), pp. 3045-3058.
Ro, et al., "Production of the Antimalarial Drug Precursor Artemisinic Acid in Engineered Yeast," Nature, vol. 440, (2006), pp. 940-943.
Sun et al., "De novo Sequencing and Analysis of the American Ginseng Root Transcriptome using a GS FLX Titanium Platform to Discover Putative Genes Involved in Ginsenoside Biosynthesis," BMC Genomics, 11:262, (2010), pp. 1-12.
Yue et al., "Purification and characterization of UDPG:ginsenoside Rd glucosyltransferase from suspended cells of Panax notoginseng," Process Biochemisry, vol. 40, pp. 3742-3748, 2005.
Notice of Allowance, Korean Patent Office, Application No. 10-2014-0125149, dated Jun. 21, 2017.

* cited by examiner

*Primary Examiner* — David Steadman
(74) *Attorney, Agent, or Firm* — Gavrilovich, Dodd & Lindsey LLP

(57) ABSTRACT

Provided are a novel UDP-glycosyltransferase (uridine diphosphate glycosyltransferase) protein having glycosyltransfer activity for glucose linked by a glycosidic bond at the C-20 position of PPD (protopanaxadiol)-type or PPT (protopanaxatriol)-type ginsenoside, and use thereof.

12 Claims, 11 Drawing Sheets

SEQUENCE LISTING

<160> NUMBER OF SEQ ID NOS: 4

<210> SEQ ID NO 1
<211> LENGTH: 449
<212> TYPE: PRT

<213> ORGANISM: Gynostemma pentaphyllum

<400> SEQUENCE: 1

```
Met Lys Lys Ile Leu Met Phe Pro Trp Leu Ala Phe Gly His Ile Ser
1               5                   10                  15

Pro Phe Leu Glu Met Ala Lys Arg Leu Ser Lys Phe Asn Phe His Ile
            20                  25                  30

Tyr Ile Cys Ser Ser Pro Ile Asn Leu Gln Ser Ile Lys Pro Lys Leu
        35                  40                  45

Ser Asp Glu Tyr Ser Ser Ser Ile Glu Leu Ile Glu Ile His Leu Pro
50                  55                  60

Ser Leu Pro Asp Leu Pro Pro His Leu His Thr Thr Asn Gly Leu Ser
65                  70                  75                  80

Ser His Leu Met Pro Thr Leu Leu Lys Ala Phe Asp Met Ser Ala Pro
                85                  90                  95

Glu Phe Thr Thr Ile Leu His Asn Leu Lys Pro Asp Leu Leu Ile Asn
            100                 105                 110

Asp Ile Leu Gln Pro Trp Ala Thr Gln Ile Ala Ser Ser Leu Asn Ile
        115                 120                 125

Pro Val Thr His Phe Ile Thr Ala Gly Val Ile Thr Leu Gly Phe Ala
130                 135                 140

Leu Gln Ser His Asn Pro Glu Ile Pro Ile Pro Asp Val Asp Leu Gly
145                 150                 155                 160

Tyr His Trp Phe Phe Lys Lys Met Ile Asn Ser Gly Ala Ser Glu Glu
                165                 170                 175

Pro Asp Ser Asp Ser Asn Leu Asn Arg Leu Trp Lys Thr Leu Val Gly
            180                 185                 190

Leu Gly His Leu Ser Asn Thr Ile Leu Ala Asn Thr Phe Thr Glu Leu
        195                 200                 205

Glu Ser Asp His Ile Asn Tyr Leu Ser Leu Leu Asn Lys Lys Val
210                 215                 220

Leu Pro Ile Gly Pro Leu Val Gln Lys Leu Thr Ser Ile Pro Asn Pro
225                 230                 235                 240

Asn Asp Glu Glu Lys Lys Pro Glu Pro Leu Glu Trp Leu Asp Lys Lys
                245                 250                 255

Ser Pro Lys Ser Thr Val Tyr Val Ser Phe Gly Ser Cys Tyr Leu
            260                 265                 270

Ser Lys Glu Gly Met Glu Glu Leu Ser His Gly Leu Glu Gln Ser Gly
        275                 280                 285

Ala Asn Phe Ile Trp Val Ile Arg Phe Pro Lys Gly Glu Lys Lys Thr
290                 295                 300

Met Arg Asp Glu Leu Pro Glu Gly Tyr Leu Glu Arg Val Gly Glu Arg
305                 310                 315                 320

Gly Met Val Ile Glu Gly Trp Ala Pro Gln Met Arg Ile Leu Glu His
                325                 330                 335

Ser Ser Val Gly Gly Phe Val Ser His Cys Gly Trp Asn Ser Met Ala
            340                 345                 350

Glu Ala Ala Val Ile Gly Val Pro Ile Ala Leu Pro Met Gln Leu
        355                 360                 365

Asp Gln Pro Trp Asn Gly Lys Ile Ala Glu Gln Cys Gly Ile Gly Val
370                 375                 380

Val Ala Lys Arg Gly Glu Glu Gly Glu Ile Met Arg Glu Glu Ile Arg
385                 390                 395                 400
```

```
Glu Val Ile Lys Glu Val Val Phe Glu Glu Lys Gly Glu Lys Met Arg
            405                 410                 415
Lys Lys Val Lys Glu Ile Ser Ala Val Leu Lys Glu Lys Glu Gly Glu
            420                 425                 430
Ile Thr Asp Gly Leu Val Asn Glu Leu Asn Leu Leu Cys Gln Ala Lys
        435                 440                 445
Ile
```

<210> SEQ ID NO 2
<211> LENGTH: 1350
<212> TYPE: DNA
<213> ORGANISM: Gynostemma pentaphyllum

<400> SEQUENCE: 2

```
atgaagaaaa ttttgatgtt tccatggttg gcttttggcc atatctcacc atttctagag     60
atggcaaaga ggctgtctaa gttcaatttt cacatttaca tttgttcttc accaataaac    120
cttcaatcca ttaaaccaaa actctcagat gaatattctt cttccattga attgatagag    180
attcatcttc catctttacc agatcttcct cctcacttgc acactaccaa tggcttatct    240
tctcatttaa tgccaacttt gttgaaagcc tttgacatgt ctgcccctga attcaccacc    300
attttacata atcttaaacc agattactc atcaatgaca ttttacaacc atgggctact    360
caaatagctt cctccctcaa tatccctgtt actcatttca ttacagctgg tgttattact    420
ctcggttttg ctctccagtc tcacaatcct gaaatcccga taccgacgt ggatctgggt    480
tatcactggt tcttcaagaa gatgataaat tcaggagctt ctgaagaacc agattccgat    540
tctaatttga atcgcttgtg gaaaacctta gttggtttag acatttatc aaacaccatt    600
cttgcaaaca cttttactga attagaaagt gatcacatca attatctctc tctgttgtta    660
aacaagaagg ttcttccaat tggaccttta gttcagaaac tcacctcaat tccaaatcca    720
aacgacgaag aaaagaaacc agaacccta gaatggcttg ataagaaaag ccctaaatca    780
acagtttacg tttcgtttgg gagcgaatgt tacctttcaa agagggcat ggaagagtta    840
tcacatggat tagaacaaag cggggcgaat ttcatatggg taattaggtt tccgaaagga    900
gaaaagaaaa cgatgagaga tgaattaccg gaaggttatt tagaaagagt tggagaaaga    960
gggatggtaa ttgaaggatg ggcaccacag atgagaattc tagagcattc tagcgtcgga   1020
gggttcgtca gtcattgtgg atggaattca atggcggaag cggcggtgat aggagtaccg   1080
atcatcgctt tgccgatgca gcttgatcag ccatggaatg ggaaaattgc agaacaatgc   1140
ggcattggtg tggtggcgaa gagagggaa gaaggagaaa taatgagaga ggaaataagg   1200
gaagtcatta agaagtggt atttgaagaa aaggagaga aatgagaaa gaaagtgaaa   1260
gagattagtg cagtgttgaa ggagaaagag ggtgaaatca cagatgggtt ggtgaatgag   1320
ttgaatttgc tttgtcaagc aaaaatataa                                   1350
```

<210> SEQ ID NO 3
<211> LENGTH: 33
<212> TYPE: DNA
<213> ORGANISM: Artificial Sequence
<220> FEATURE:
<223> OTHER INFORMATION: GpUGT23-F primer

<400> SEQUENCE: 3

```
gatcggatcc atgaagaaaa ttttgatgtt tcc                                 33
```

<210> SEQ ID NO 4

```
<211> LENGTH: 29
<212> TYPE: DNA
<213> ORGANISM: Artificial Sequence
<220> FEATURE:
<223> OTHER INFORMATION: GpUGT23-R primer

<400> SEQUENCE: 4
gatcctcgag tatttttgct tgacaaagc                                         29
```

GLYCOSYLTRANSFERASE DERIVED FROM DOLWOE AND USE THEREOF

CROSS REFERENCE TO RELATED APPLICATIONS

This application claims priority under 35 U.S.C. § 119 to Korean Patent Application No. 10-2014-0125149, filed Sep. 19, 2014, the disclosure of which is incorporated herein by reference.

BACKGROUND OF THE INVENTION

1. Field of the Invention

The present invention relates to a novel UDP-glycosyltransferase (uridine diphosphate glycosyltransferase) protein having glycosyltransfer activity for glucose linked by a glycosidic bond at the C-20 position of a PPD (protopanaxadiol)-type or PPT (protopanaxatriol)-type ginsenoside, and use thereof.

2. Description of the Related Art

Ginsenosides are glycosylated dammarene-type tetracyclic triterpenes, and they can be classified into three different groups based on their aglycone structure: protopanaxadiol (PPD)-type ginsenosides, protopanaxatriol (PPT)-type ginsenosides, and oleanolic acid-type ginsenosides. These three groups can be further classified based on the position and number of sugar moieties (aglycones) attached to the C-3, C-6, and C-20 positions of the rings by a glycosidic bond in the chemical structure. PPD and PPT also possess different hydroxylation patterns. PPD possesses —OH groups at the C-3, C-12, and C-20 positions, whereas PPT possesses —OH groups at the C-3, C-6, C-12, and C-20 positions. PPD and PPT can be glycosylated with glucose and other types of sugars to be converted into various ginsenosides. The representative PPD-type ginsenosides include ginsenoside $Rb_1$, Rd, F2, $Rg_3$, $Rh_2$, CK (Compound K), $Rb_2$, Rc, C-MC (Compound MC), and C-Y (Compound Y), and the representative PPT-type ginsenosides include $Rg_1$, $Rh_1$, F1, Rf, Re, and $Rg_2$.

Meanwhile, the biosynthetic pathway of ginsenosides has only been partially identified. The ginsenoside biosynthesis is known to share the biosynthetic pathways with other triterpenes until oxidosqualene is synthesized by a series of condensation reactions of isopentenyl diphosphate and DMADP (dimethylallyl diphosphate) by the action of IPP isomerase (IPI), GPP synthase (GPS), FPP synthase (FPS), squalene synthase (SS), and squalene epoxidase (SE) (Ajikumar et al. Science, 330, 70-74. 2010; Ro et al. Nature, 440, 940-943. 2006; Sun et al. BMC genomics, 11, 262, 2010). Oxidosqualene is cyclized into dammarenediol-II by DS (dammarenediol-II synthase) which is a triterpene cyclase. Dammarenediol-II has hydroxyl groups at the C-3 and C-20 positions, and it is converted into PPD by hydroxylation of the C-12 position by a p450 enzyme, PPDS (protopanaxadiol synthase). PPDS can be also converted into PPT by hydroxylation at the C-6 position by another p450 enzyme, PPTS (protopanaxatriol synthase). PPD can be converted into various kinds of PPD-type ginsenosides by glycosylation at the C-3 and/or C-20 position(s), and PPT can be converted into various kinds of PPT-type ginsenosides by glycosylation at the C-6 and/or C-20 position(s).

UDP (Uridine diphosphate)-glycosyltransferase (UGT) is an enzyme that catalyzes the transfer of a sugar moiety from UDP-sugar to a wide range of metabolites such as hormones and secondary metabolites. Generally, UGT acts in the final step of biosynthetic pathway in order to increase solubility, stability, storage, bioactivity, or biological availability of metabolites. As recognized by a remarkable diversity of metabolites in plants, the genome of a plant possesses hundreds of different UGTs. For example, a plant model, Arabidopsis thaliana, contains 107 UGTs that belong to 14 different groups (Group A to Group N) based on the amino acid sequence. However, DS, PPDS, and PPTS have been reported as the enzymes involved in ginsenoside biosynthesis, but it has not been identified whether UGT is involved in the biosynthesis of ginsenosides. Thus, there is a need to investigate UGT that utilizes a ginsenoside as a substrate in order to produce a particular ginsenoside.

Further, different UGTs show substrate specificity towards both sugar donor and sugar acceptors. For example, UGT78D2 transfers glucose from UDP-glucose to the C-3 position of flavonol (kaempferol, quercetin) and anthocyanin (cyanidin) to produce flavonol 3-O-glucosides and cyanidin 3-O-glucoside, respectively. It seems that such glycosylation is essential for in vivo stability and storage of the compound. On the other hand, UGT89C1 transfers rhanmnose from UDP-rhanmnose to the C-7 position of flavonol-3-O-glucosides to produce flavonol-3-O-glucoside-7-O-rhamnoside. Likewise, UGT89C1 does not utilize UDP-glucose and anthocyanin-3-O-glucoside as a substrate, and it has different specificity towards UDP-sugars and acceptors from that of UGT78D2. As such, UGTs are different from each other in terms of substrate specificity and regioselectivity, and therefore, there is a need to investigate the substrate specificity and regioselectivity of different types of UGTs.

With this background, the present inventors have made many efforts to develop a novel UDP-glycosyltransferase with substrate specificity and regioselectivity which can be used for biosynthesis of a particular ginsenoside. As a result, the present inventors identified a novel glycosyltransferase GpUGT23 from Dolwoe (Gynostemma pentaphyllum), and they found that GpUGT23 has glycosyltransfer activity for glucose linked by a glycosidic bond at the C-20 position of PPD-type and PPT-type ginsenosides, and GpUGT23 can be used for the production of particular ginsenosides such as gypenoside LXXV, gypenoside XVII, $Rb_1$, notoginsenoside U, notoginsenoside R3 or gluco-Re, thereby completing the present invention.

SUMMARY OF THE INVENTION

An object of the present invention is to provide a method of preparing a PPD- or PPT-type ginsenoside by transferring a sugar to glucose linked by a glycosidic bond at the C-20 position using a UDP-glycosyltransferase protein having glycosyltransfer activity for glucose linked by a glycosidic bond at the C-20 position of a PPD (protopanaxadiol)-type or PPT (protopanaxatriol)-type ginsenoside; a vector including a polynucleotide encoding the protein; a transformant introduced with the vector; or a culture of the transformant.

Another object of the present invention is to provide a composition for transferring a sugar to a PPD-type or PPT-type ginsenoside having glucose linked by a glycosidic bond at the C-20 position, including the UDP-glycosyltransferase protein; the vector including the polynucleotide encoding the protein; the transformant introduced with the vector; or the culture of the transformant as an active ingredient.

Still another object of the present invention is to provide a UDP-glycosyltransferase protein having glycosyltransfer activity selective for glucose linked by a glycosidic bond at the C-20 position of a PPD-type or PPT-type ginsenoside.

Still another object of the present invention is to provide a polynucleotide encoding the protein, an expression vector including the polynucleotide, and a transformant including the expression vector.

DETAILED DESCRIPTION OF THE PREFERRED EMBODIMENTS

Figure 1:
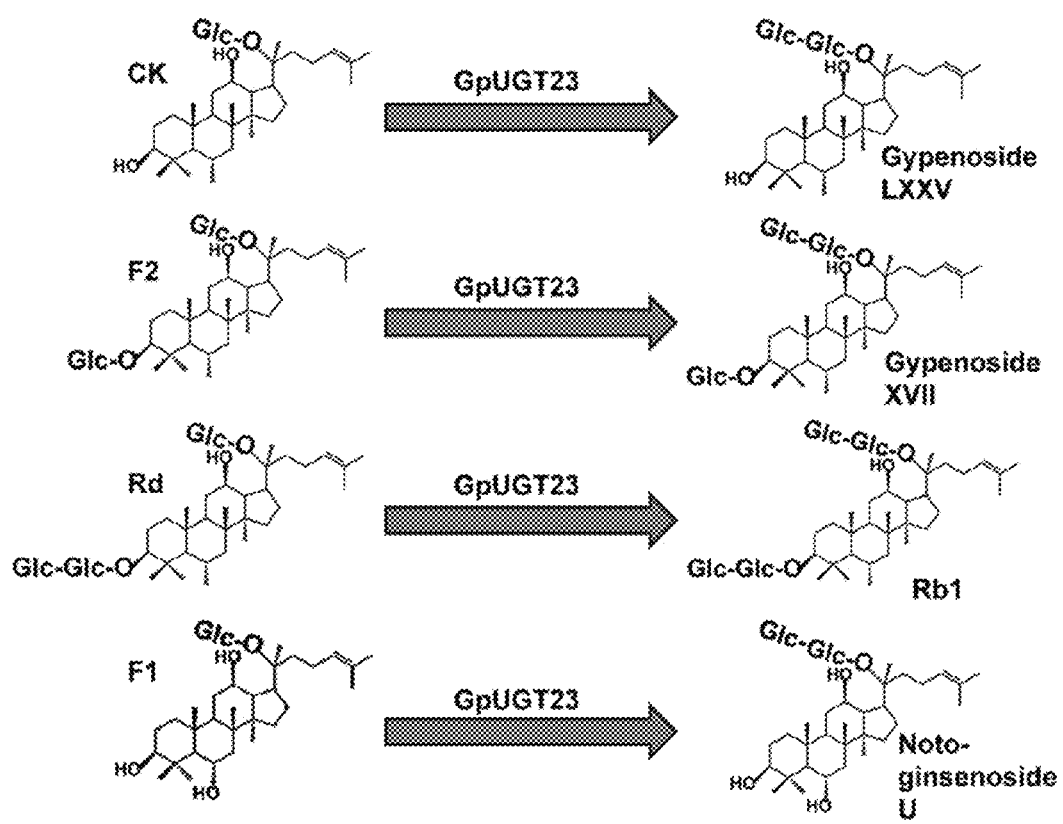
FIG. 1 illustrates PPD-type and PPT-type ginsenosides glycosylated by GpUGT23 of the present invention.

In order to achieve the above objects, an aspect of the present invention provides a method of preparing a PPD- or PPT-type ginsenoside glycosylated at glucose linked by a glycosidic bond at the C-20 position using a UDP-glycosyltransferase protein having glycosyltransfer activity for glucose linked by a glycosidic bond at the C-20 position of a PPD (protopanaxadiol)-type or PPT (protopanaxatriol)-type ginsenoside; a vector including a polynucleotide encoding the protein; a transformant introduced with the vector; or a culture of the transformant.

As used herein, the term "UDP (uridine diphosphate)-glycosyltransferase" is an enzyme that catalyzes the transfer of a monosaccharide moiety from a glycosyl donor to a glycosyl acceptor molecule, and in particular, it refers to an enzyme that utilizes a UDP-sugar as the glycosyl donor. In the present invention, the UDP-glycosyltransferase may be interchangeably used with UGT. Very little is known about the ginsenoside UDP-glycosyltransferase. Even though those enzymes have the UDP-glycosyltransferase activity, they have different substrate specificity and regioselectivity depending on the type of the enzyme. Therefore, it needs to be determined whether the enzyme is a UDP-glycosyltransferase specifically acting on a ginsenoside, which is a ginseng saponin.

In the present invention, a novel UDP-glycosyltransferase derived from Dolwoe (*Gynostemma pentaphyllum*) was identified for the first time, in which the UDP-glycosyltransferase is able to selectively transfer a sugar moiety to glucose linked by a glycosidic bond at the C-20 position of a PPD-type ginsenoside and a PPT-type ginsenoside. The UDP-glycosyltransferase identified in the present invention has activity for selectively transferring a sugar moiety of UDP-glucose to glucose linked by a glycosidic bond at the C-20 position of a PPD-type ginsenoside or a PPT-type ginsenoside. Therefore, the UDP-glycosyltransferase identified in the present invention may be, but is not particularly limited to, a UDP-glycosyltransferase capable of converting PPD-type ginsenosides, CK, F2, and Rd into gypenoside LXXV (interchangeably used with Gyp 75), gypenoside XVII (interchangeably used with Gyp 17), and ginsenoside $Rb_1$, respectively, or converting PPT-type ginsenosides, F1, $Rg_1$, and Re into notoginsenoside U, notoginsenoside R3, and gluco-Re, respectively, by transferring a sugar moiety to glucose linked by a glycosidic bond at the C-20 position thereof. There have been no reports about ginsenoside UDP-glycosyltransferase having this activity, which was identified by the present inventors for the first time.

The UDP-glycosyltransferase identified in the present invention is a UDP-glycosyltransferase derived from Dolwoe, and it may include an amino acid sequence represented by SEQ ID NO: 1. The UDP-glycosyltransferase may be defined by this amino acid sequence. In an embodiment of the present invention, the UDP-glycosyltransferase defined by the amino acid sequence of SEQ ID NO: 1 is designated as 'GpUGT23'.

The UDP-glycosyltransferase of the present invention may be a protein having the amino acid sequence of SEQ ID NO: 1, but also an amino acid sequence having a sequence homology of 70% or higher, specifically 80% or higher, more specifically 90% or higher, even more specifically 95% or higher, even much more specifically 98% or higher, and most specifically 99% or higher to the amino acid sequence of SEQ ID NO. 1, as long as it has the activity capable of substantially transferring a sugar to glucose linked by a glycosidic bond at the C-20 position of a PPD-type ginsenoside or a PPT-type ginsenoside. In addition, if an amino acid sequence has a biological activity substantially the same as or corresponding to UDP-glycosyltransferase, protein variants prepared by deletion, modification, substitution, or addition of a portion of the amino acid sequence of SEQ ID NO: 1 may be included in the scope of the present invention.

As used herein, the term "homology" refers to a percentage of similarity between two polypeptides or polypeptide moieties. The homology between sequences from one moiety to another moiety may be determined by techniques known in the art. For example, homology may be determined by a direct comparison of the sequence information between two polynucleotide molecules or two polypeptide molecules by aligning the sequence information and using readily available computer programs. The computer program may be BLAST (NCBI), CLC Main Workbench (CLC bio), MEGALIGN™ (DNASTAR Inc), but any program may be used without limitation, as long as it is used to determine homology. Alternatively, homology between polynucleotides may be determined by hybridization of polynucleotides under conditions which allow formation of stable duplexes between homologous regions, followed by digestion with single stranded-specific nuclease(s), and then by size determination of the digested fragments, but is not limited thereto.

The UDP-glycosyltransferase of the present invention has glycosyltransfer activity selective for glucose linked by a glycosidic bond at the C-20 position of PPD-type or PPT-type ginsenoside, and thus this is applied to a PPD-type or PPT-type ginsenoside having glucose linked by a glycosidic bond at the C-20 position, thereby preparing a glycosylated ginsenoside.

As used herein, the term "PPD-type or PPT-type ginsenoside having glucose linked by a glycosidic bond at the C-20 position" refers to a ginsenoside in which a sugar is covalently linked with a —OH group at the C-20 position of a PPD-type or PPT-type ginsenoside. The sugar may be, but is not particularly limited to, specifically glucose, and a ginsenoside having a glycosidic bond at the C-20 position may have O-glucoside at the C-20 position. An example of the PPD-type or PPT-type ginsenoside having glucose covalently linked with a —OH group at the C-20 position may include CK (compound K), F2, Rd, F1, $Rg_1$, or Re, but is not limited thereto.

As used herein, the term "PPD-type ginsenoside" is a dammarane-type saponin, and it means a PPD possessing —OH groups at the C-3, C-12, and C-20 positions, or a ginsenoside glycosylated at one or more —OH groups of PPD.

As used herein, the term "PPT-type ginsenoside" is a dammarane-type saponin, and it means a PPT possessing —OH groups at the C-3, C-6, C-12, and C-20 positions, or a ginsenoside glycosylated at the —OH group of PPT.

The PPD-type or PPT-type ginsenoside may be a ginsenoside in an isolated and purified form, or a ginsenoside contained in a powder or an extract of a plant, for example, ginseng or red ginseng. That is, the powder or extract of ginseng or red ginseng containing saponin may be directly used as the ginsenoside to perform the method of the present invention. Further, chemically synthesized ginsenoside may be used. The ginseng used in the present invention includes the known various types of ginsengs, such as *Panax ginseng, P. quiquefolius, P. notoginseng, P. japonicus, P. trifolium, P. pseudoginseng*, and *P. vietnamensis*, but is not limited thereto.

As used herein, the term "PPD-type or PPT-type ginsenoside glycosylated at glucose linked by a glycosidic bond at the C-20 position" is a glycosylated ginsenoside prepared by transferring a sugar, preferably glucose, to glucose linked by a glycosidic bond at the C-20 position of a PPD-type or PPT-type ginsenoside, and examples thereof may include gypenoside LXXV, gypenoside XVII, $Rb_1$, notoginsenoside U, notoginsenoside R3, or gluco-Re, but are not limited thereto.

As used herein, the term "gluco-Re" means a ginsenoside glycosylated at glucose linked by a glycosidic bond at the C-20 position of the ginsenoside Re.

Further, in the preparation of glycosylated ginsenoside by converting a PPD-type or PPT-type ginsenoside having glucose linked by a glycosidic bond at the C-20 position, an expression vector including a polynucleotide encoding the UDP-glycosyltransferase, a transformant introduced with the vector, or a culture of the transformant may be used.

The polynucleotide encoding the UDP-glycosyltransferase protein may preferably be a polynucleotide represented by a nucleotide sequence of SEQ ID NO: 2, and it may also be any nucleotide sequence having a sequence homology of 70% or higher, specifically 80% or higher, more specifically 90% or higher, much more specifically 95% or higher, and most specifically 98% or higher to the nucleotide sequence of SEQ ID NO: 2 without limitation, as long as it is able to substantially encode a protein having the GpUGT23 protein activity. Further, due to genetic code degeneracy, a base sequence encoding the amino acid sequence of SEQ ID NO: 1 and variants thereof are also included in the present invention.

The expression vector including the polynucleotide of the present invention is an expression vector capable of expressing the desired protein in a suitable host cell, and refers to a DNA construct including essential regulatory elements which are operably linked to express a nucleic acid insert. The desired proteins may be obtained by transformation or transfection of the prepared recombinant vector into the host cells.

The expression vector including the polynucleotide provided in the present invention may include, but is not particularly limited to, *E. coli*-derived plasmids (pYG601BR322, pBR325, pUC118, and pUC119), *Bacillus subtilis*-derived plasmids (pUB110 and pTP5), yeast-derived plasmids (YEp13, YEp24, and YCp50), and Ti-plasmids used in *Agrobacterium*-mediated transformation. The specific example of phage DNA includes λ-phage (Charon4A, Charon21A, EMBL3, EMBL4, λgt10, λgt11, and λZAP). Further, an animal virus such as retrovirus, adenovirus, or vaccinia virus, an insect virus such as baculovirus, a double-stranded plant virus (e.g., CaMV), a single-stranded virus, or a viral vector originated from Geminivirus may be used.

Moreover, as the vector of the present invention, a transcriptional activator, such as B42-linked fusion plasmid (e.g., pJG4-5), may be used. In order to facilitate purification of the desired protein obtained in the present invention, the plasmid vector may further include other sequences, if necessary. The fusion plasmid may include a tag such as GST, GFP, His-tag, Myc-tag, or the like, but the fusion plasmid of the present invention is not limited to these examples.

In addition, the preparation of the fusion protein may include a chromatography process, and the fusion protein may be purified by affinity chromatography. For example, if glutathione-S-transferase is fused, glutathione, which is a substrate of the enzyme, may be used. If hexa-histidine is used, the desired protein may be easily purified by using a Ni-NTA His-bind resin column (Novagen, USA).

For insertion of the polynucleotide of the present invention into the vector, the purified DNA may be cleaved using appropriate restriction enzymes and inserted into the restriction sites or cloning site of a suitable vector DNA.

The polynucleotide encoding the UDP-glycosyltransferase protein of the present invention may be operably linked to a vector. The vector of the present invention may further include cis elements such as an enhancer, a splicing signal, a poly A addition signal, a selection marker, and a ribosome binding sequence (SD sequence) in addition to a promoter and the nucleic acid of the present invention. As examples of the selection marker, a chloramphenicol resistance gene, an ampicillin resistance gene, dihydrofolate reductase, a neomycin resistance gene, or the like may be used, but the type of additional elements to be operably linked is not limited to these examples. As used herein, the term "transformation" means an introduction of DNA into a host cell such that DNA can be replicated as an extra-chromosomal element or by chromosomal integration. That is, transformation refers to synthetic alteration of genes by introducing a foreign DNA into the cell.

By the transformation, the expression vector including the polynucleotide encoding the UDP-glycosyltransferase protein of the present invention or a part of the expression vector may be introduced into a host cell. Herein, the part of the expression vector means a part of the expression vector including a part of the polynucleotide encoding the UDP-glycosyltransferase protein to provide the host cell with the UDP-glycosyltransferase protein activity. It may be exemplified by T-DNA of Ti-plasmid transferred into the host cell in *Agrobacterium*-mediated transformation, but is not limited thereto.

The transformation of the present invention may be performed by any transformation method, and may be easily performed following the common methods known in the art. In general, examples of the transformation method include a CaCl$_2$ precipitation, a Hanahan method that is an improved CaCl$_2$ method by using DMSO (dimethyl sulfoxide) as a reducing material, electroporation, calcium phosphate precipitation, protoplast fusion, agitation using silicon carbide fiber, *Agrobacterium*-mediated transformation, PEG-mediated transformation, and dextran sulfate-, lipofectamine-, and desiccation/inhibition-mediated transformations. The method for transformation of the vector, including the polynucleotide encoding UDP-glycosyltransferase of the present invention, is not limited to these examples, and the transformation or transfection methods commonly used in the art may be used without limitation.

In the present invention, the type of host cell is not particularly limited, as long as it is able to express the polynucleotide of the present invention. The specific examples of the host cell to be used in the present invention include bacteria belonging to the genus *Escherichia* such as *E. coli*; bacteria belonging to the genus *Bacillus* such as *Bacillus subtilis*; bacteria belonging to the genus *Pseudomonas* such as *Pseudomonas putida*; yeasts such as *Saccharomyces cerevisiae* and *Schizosaccharomyces pombe*; animal cells; plant cells; and insect cells. The specific examples of the *E. coli* strain to be used in the present invention include CL41(DE3), BL21, or HB101, and the specific examples of the *Bacillus subtilis* strain include WB700 and LKS87.

The transformant introduced with the expression vector including the polynucleotide of the present invention may be a transformed cell or organism. Examples of the organism may include, but are not particularly limited to, tobacco, *Arabidopsis thaliana*, potato, ginseng, sesame, citron, Bellis, or the like.

Any promoter may be used as a promoter of the present invention, as long as it is able to drive expression of the nucleic acid of the present invention in the host cell. For example, *E. coli*- or phage-derived promoters such as trp promoter, lac promoter, PL promoter, and PR promoter; and *E. coli* infection phage-derived promoters such as T7 promoter, CaMV35S, MAS, or histone promoter may be used. Synthetically modified promoters such as tac promoter may also be used.

The transformant that is introduced with the expression vector including the polynucleotide encoding the UDP-glycosyltransferase protein of the present invention by the above method has glycosyltransfer activity selective for a glucose linked by a glycosidic bond at the C-20 position of a PPD-type or PPT-type ginsenoside. For example, the transformant has one or more transfer activities selected from the group consisting of conversion of CK into gypenoside LXXV, conversion of F2 into gypenoside XVII, conversion of Rd into Rb$_1$, conversion of F1 into notoginsenoside U, conversion of Rg$_1$ into notoginsenoside R3, and conversion of Re into gluco-Re, but is not limited thereto.

As used herein, the term "culture of the transformant" means a product obtained by culturing the transformant. The culture is a concept including all of a culture containing the transformant and a culture obtained by removing the transformant from the culture medium containing the transformant by centrifugation.

The culture includes the UDP-glycosyltransferase protein of the present invention, and thus it has activity for converting a PPD-type or PPT-type ginsenoside having glucose linked by a glycosidic bond at the C-20 position into glycosylated ginsenosides, for example, conversion of CK into gypenoside LXXV, conversion of F2 into gypenoside XVII, conversion of Rd into Rb$_1$, conversion of F1 into notoginsenoside U, conversion of Rg$_1$ into notoginsenoside R3, and conversion of Re into gluco-Re.

The UDP-glycosyltransferase protein of the present invention; the expression vector including the polynucleotide encoding the protein; the transformant introduced with the expression vector; or the culture of the transformant may be used to convert a PPD-type or PPT-type ginsenoside having glucose linked by a glycosidic bond at the C-20 position into glycosylated ginsenosides, and thus the method may be used in the fields that require glycosylated ginsenosides in which glucose linked by a glycosidic bond at the C-20 position is glycosylated, in particular, ginsenosides such as gypenoside LXXV, gypenoside XVII, Rb$_1$, notoginsenoside U, notoginsenoside R3, and gluco-Re.

Figure 2:
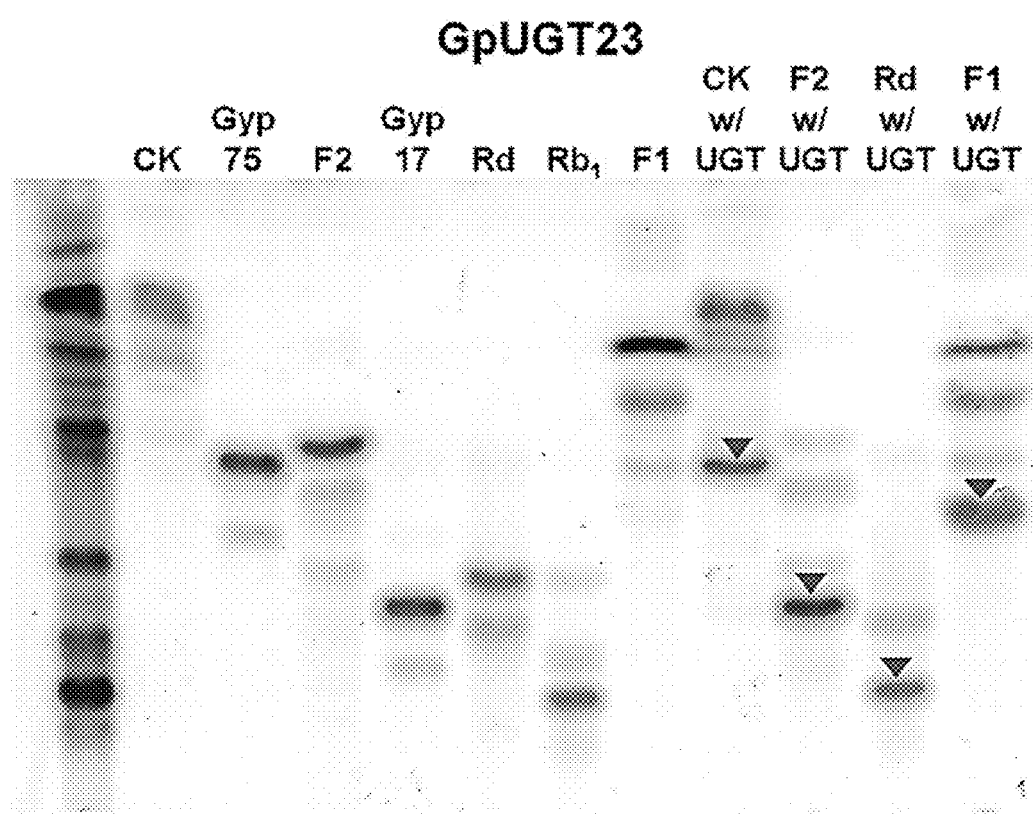
FIG. 2 shows results of thin-layer chromatography (TLC) demonstrating that the UDP-glycosyltransferase GpUGT23 has glycosyltransfer activity for glucose linked by a glycosidic bond at the C-20 position of a PPD-type or PPT-type ginsenoside, in which GpUGT23 converts CK (Compound K), F2, Rd, and F1 into gypenoside LXXV, gypenoside XVII, $Rb_1$, and notoginsenoside U, respectively.
Figure 3A:
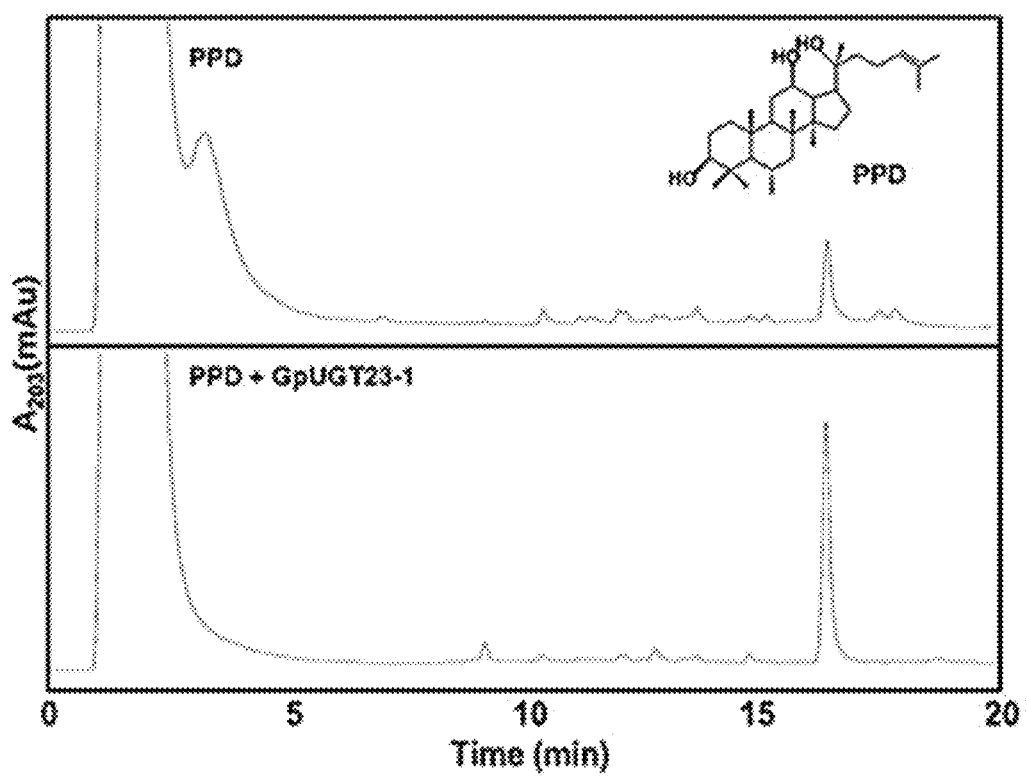
FIG. 3A-E shows results of high performance liquid chromatography (HPLC) demonstrating that the UDP-glycosyltransferase GpUGT23 shows no glycosyltransfer activity in a PPD-type or PPT-type ginsenoside having no glucose linked by a glycosidic bond at the C-20 position, in which GpUGT23 does not transfer a glucose to PPD (FIG. 3a), $Rh_2$ (FIG. 3b), $Rg_3$ (FIG. 3c), PPT (FIG. 3d), and $Rh_1$ (FIG. 3e) having no glucose linked by a glycosidic bond at the C-20 position and having only a —OH group.
Figure 3B:
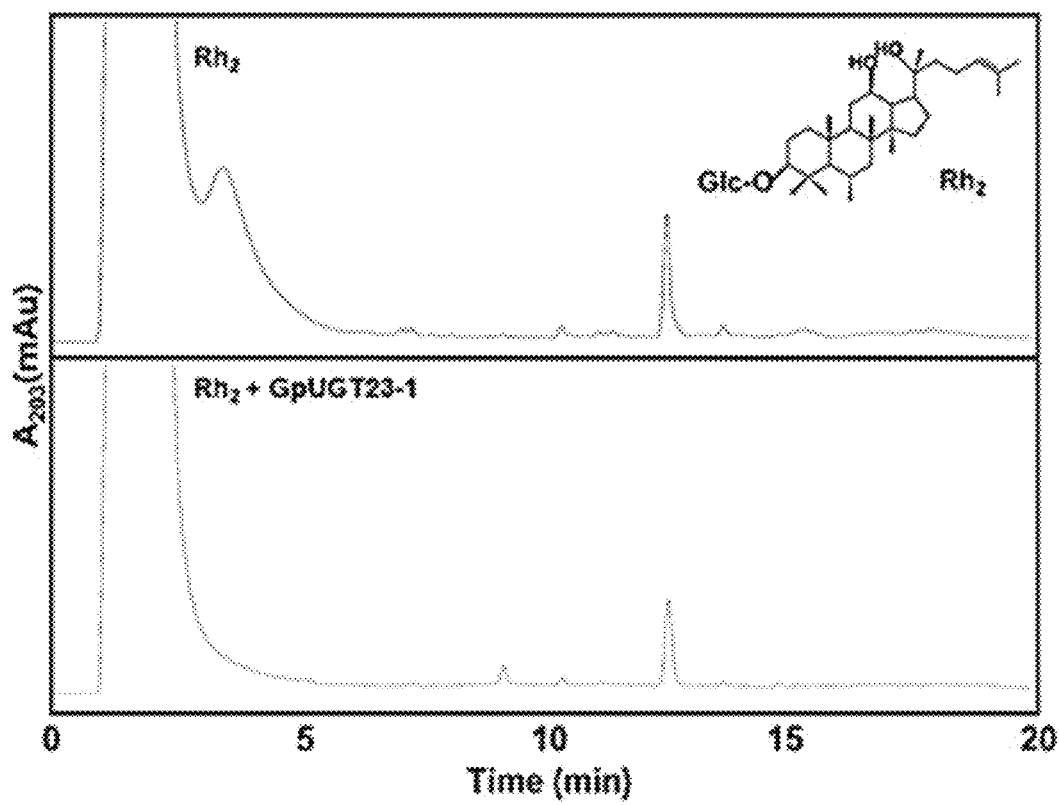
Figure 3C:
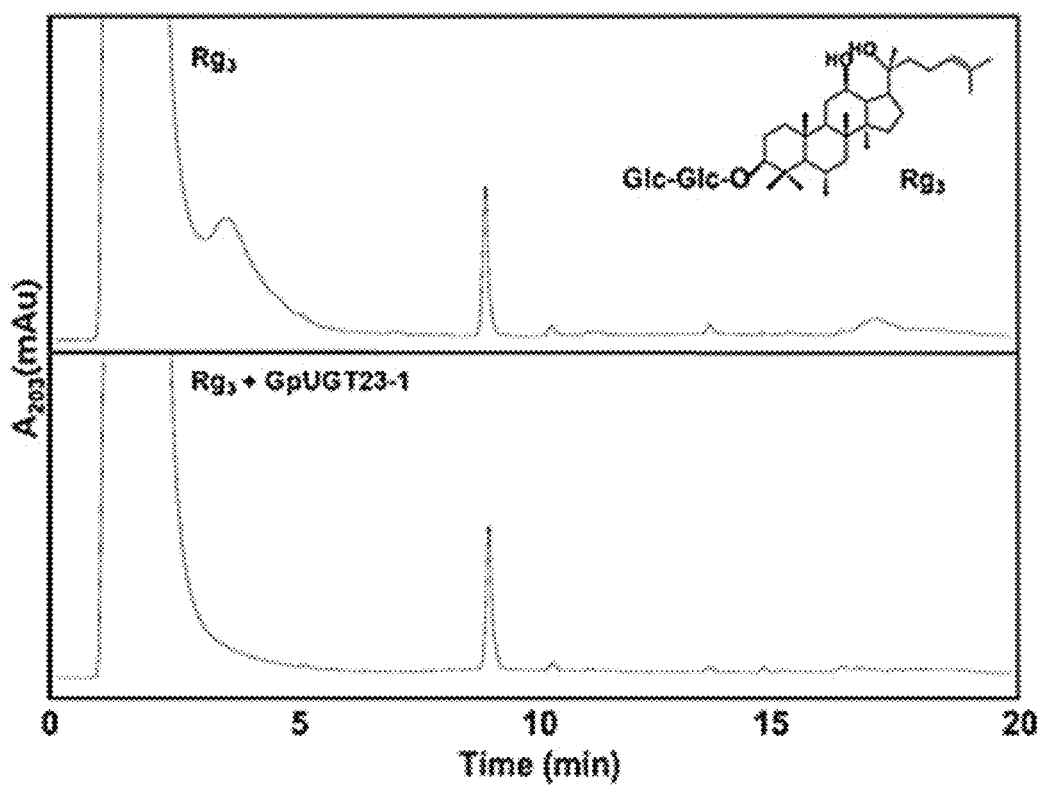
Figure 3D:
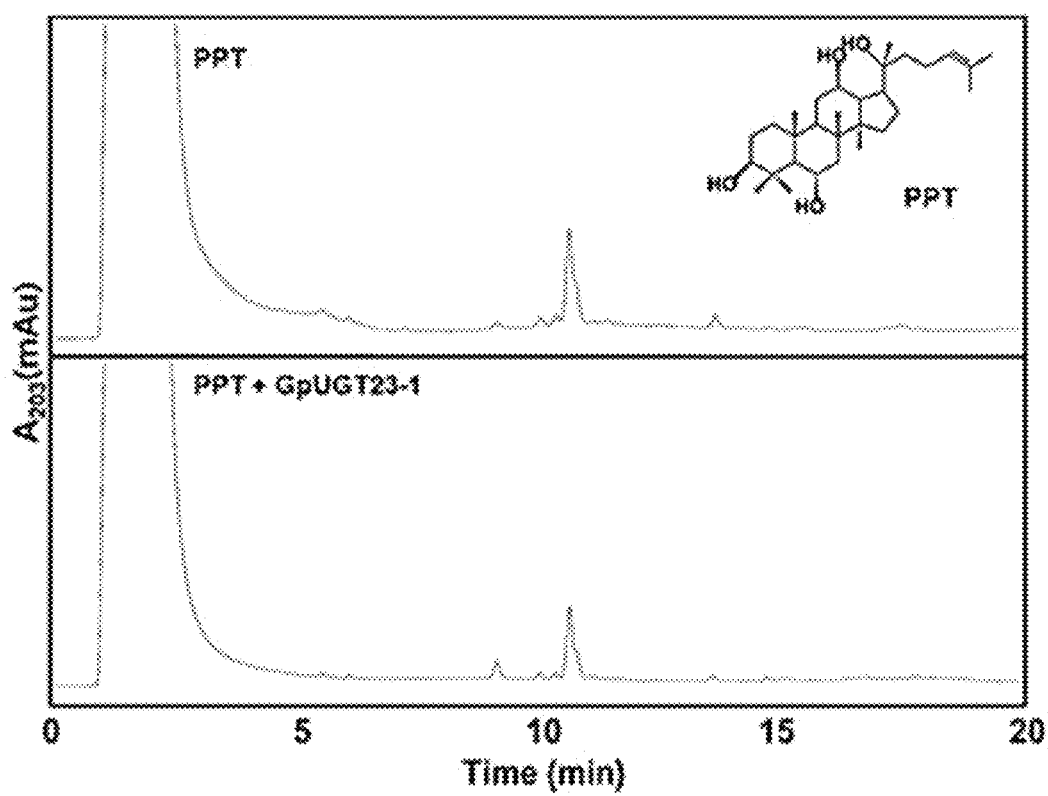
Figure 3E:
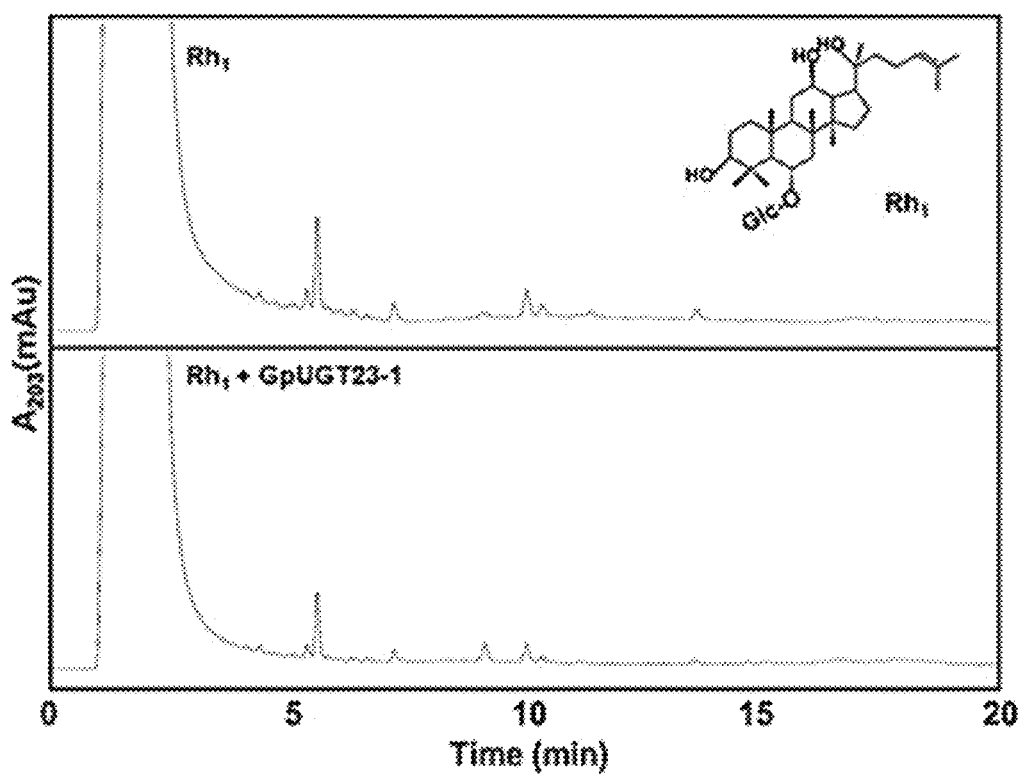
Figure 4A:
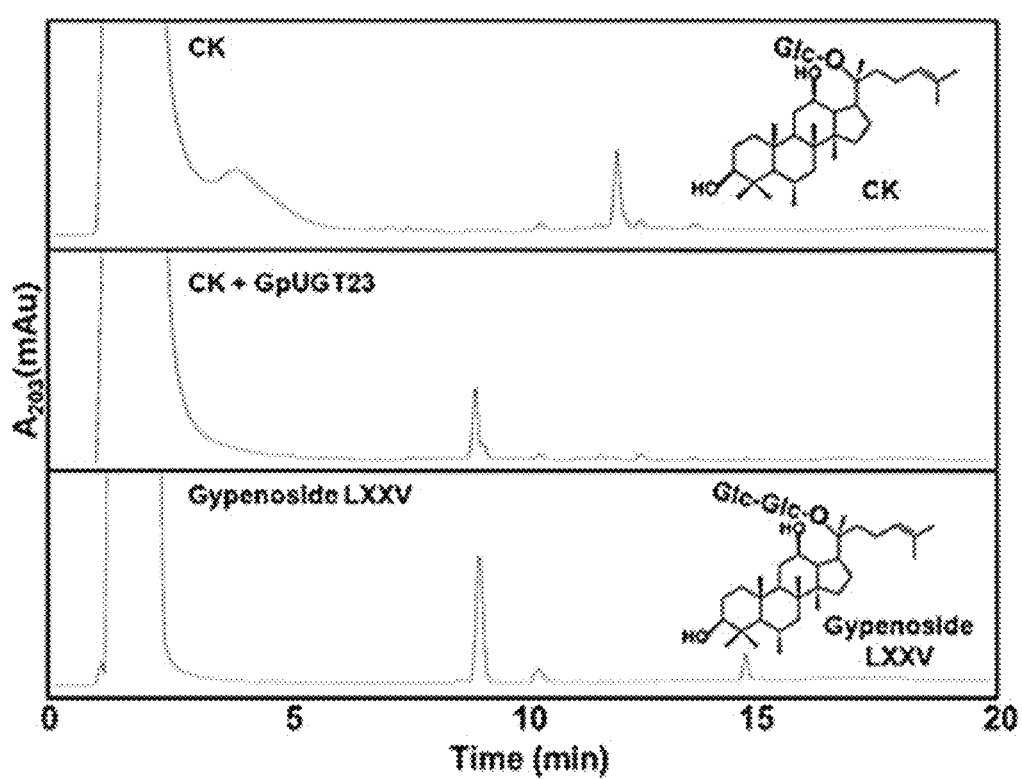
FIG. 4A-D shows results of HPLC demonstrating that GpUGT23 has glycosyltransfer activity for glucose linked by a glycosidic bond at the C-20 position of a PPD-type or PPT-type ginsenoside, in which GpUGT23 converts CK, F2, Rd, and F1 into gypenoside LXXV (FIG. 4a), gypenoside XVII (FIG. 4b), $Rb_1$ (FIG. 4c), and notoginsenoside U (FIG. 4d), respectively.
Figure 4B:
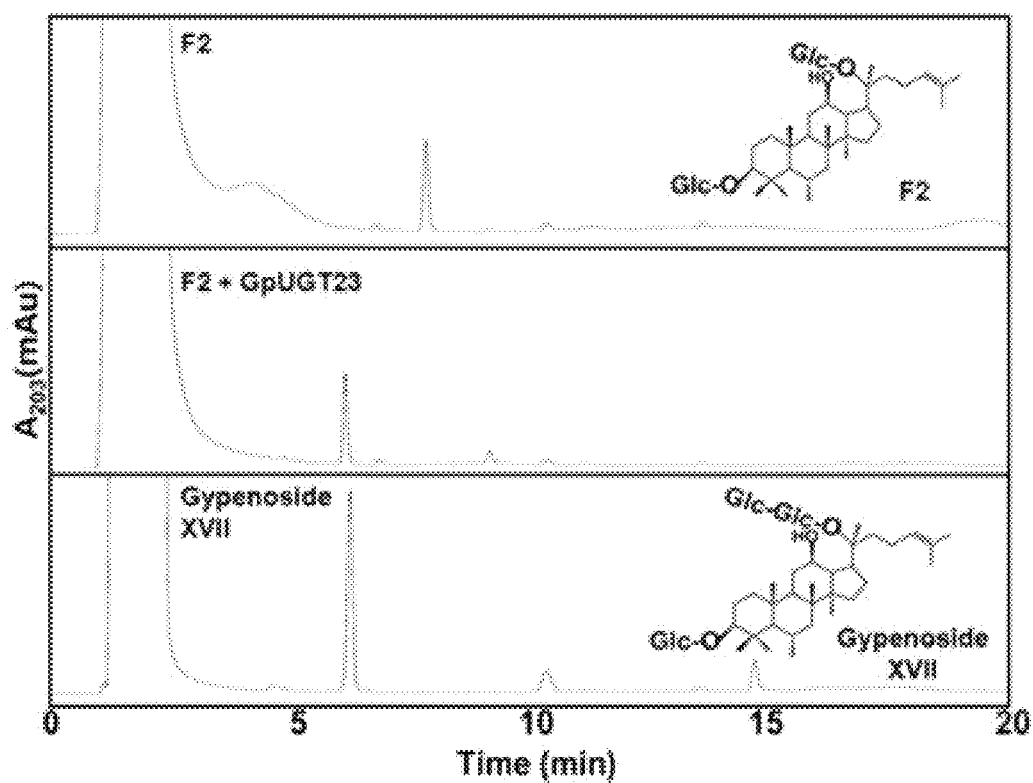
Figure 4C:
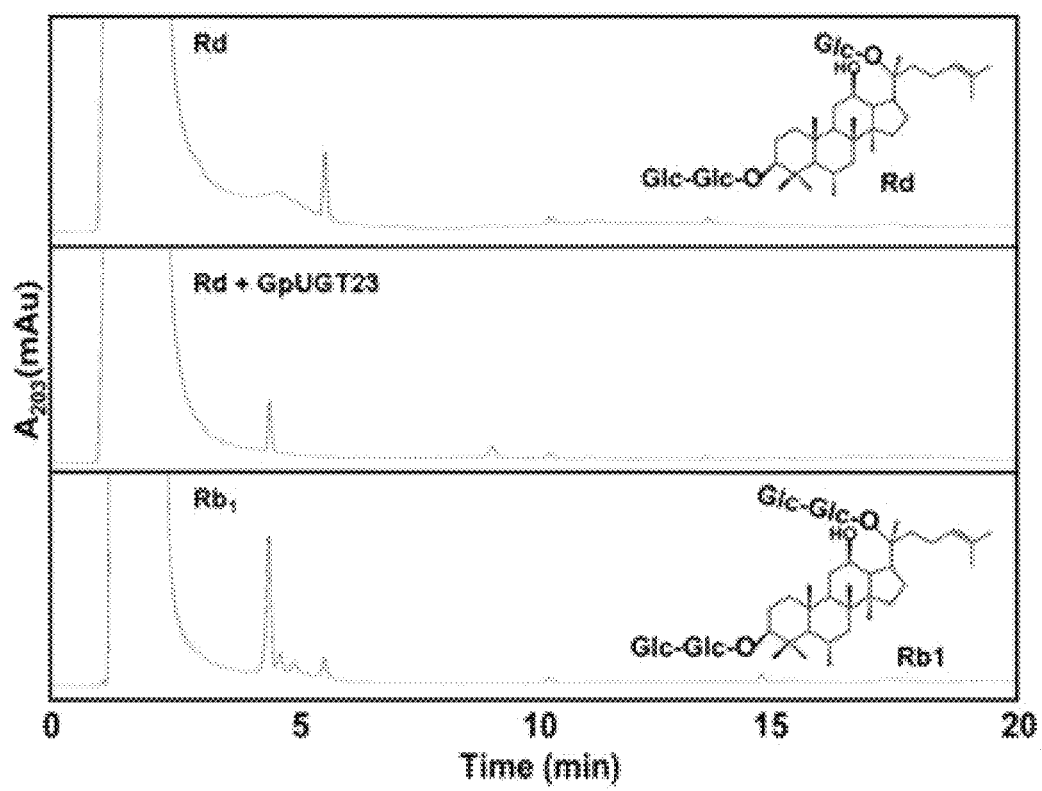
Figure 4D:
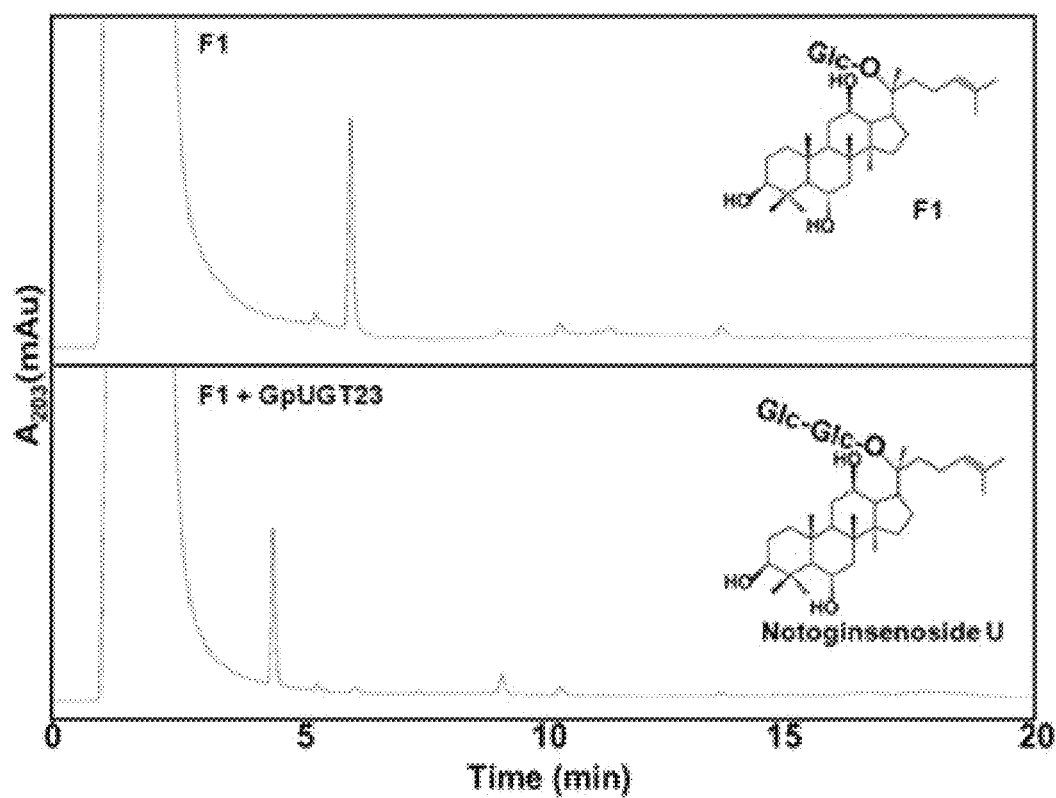

In an embodiment of the present invention, a novel UDP-glycosyltransferase was identified from Dolwoe, in which the UDP-glycosyltransferase has activity for selectively transferring a glucose moiety of UDP-glucose to glucose linked by a glycosidic bond at the C-20 position of a PPD-type and PPT-type ginsenoside, and consists of an amino acid sequence of SEQ ID NO: 1. The UDP-glycosyltransferase was designated as GpUGT23 (Example 1). To investigate the enzymatic activity of the identified GpUGT23 protein, CK, F2, Rd, and F1, which are representative PPD-type or PPT-type ginsenosides having glucose linked by a glycosidic bond at the C-20 position, were reacted with GpUGT23 of the present invention to examine their transfer activities. As a result, GpUGT23 of the present invention was found to convert CK into gypenoside LXXV, to convert F2 into gypenoside XVII, to convert Rd into Rb$_1$, and to convert F1 into notoginsenoside U (FIGS. 2 and 4). In contrast, GpUGT23 of the present invention did not transfer a sugar to PPD, Rh$_2$, Rg$_2$, PPT, and Rh$_1$, which have no glucose linked by a glycosidic bond at the C-20 position and have only a —OH group (FIG. 3). These results suggest that GpUGT23 has activity of specifically transferring a glucose moiety to a glucose linked by a glycosidic bond at the C-20 position of a PPD-type or PPT-type ginsenoside.

Another aspect of the present invention provides a composition for glycosylation of a PPD-type or PPT-type ginsenoside having glucose linked by a glycosidic bond at the C-20 position, including the UDP-glycosyltransferase protein having glycosyltransfer activity for glucose linked by a glycosidic bond at the C-20 position of a PPD-type or PPT-type ginsenoside; the vector including the polynucleotide encoding the protein; the transformant introduced with the vector; or the culture of the transformant as an active ingredient.

The UDP-glycosyltransferase protein, the vector, the transformant, the PPD-type or PPT-type ginsenoside, and the glycosylated ginsenoside are the same as described above.

Still another aspect of the present invention provides a UDP-glycosyltransferase protein having glycosyltransfer activity for glucose linked by a glycosidic bond at the C-20 position of a PPD-type or PPT-type ginsenoside.

The UDP-glycosyltransferase protein is the same as described above.

Still another aspect of the present invention provides a polynucleotide encoding the UDP-glycosyltransferase protein, an expression vector including the polynucleotide, a transformed cell including the expression vector, and an organism including the transformed cell, excluding humans.

The polynucleotide, the expression vector, the transformed cell, and the organism are the same as described above.

Hereinafter, the present invention will be described in more detail with reference to the following Examples. However, these Examples are for illustrative purposes only, and the invention is not intended to be limited by these Examples.

Example 1: Cloning and Purification of Dolwoe-Derived UDP-Glycosyltransferase GpUGT23

A gene was amplified from Dolwoe (*Gynostemma pentaphyllum*) cDNA by PCR using primers of GpUGT23-F (5'-GATCGGATCCATGAAGAAAATTTTGATGTTTCC-3'; SEQ ID NO: 3), GpUGT23-R (5'-GATCCTCGAGT-ATTTTTGCTTGACAAAGC-3'; SEQ ID NO: 4), and polymerase, and respective ends of the gene were cleaved using restriction enzymes BamHI and XhoI. Thereafter, the gene was cloned into a pET50 (Oh et al. Plant Cell, 16, 3045-3058. 2004) vector to prepare an expression vector, which was transformed into *E. coli* BL21(DE3)-RIL strain to prepare a GpUGT23-expressing strain. The protein expression in this strain was induced by IPTG to obtain the protein, which was purified using a Ni-NTA His-binding resin to purify GpUGT23 enzyme.

Example 2: In Vitro Enzyme Assay

A glycosyltransferase assay was performed in a reaction buffer (10 mM PBS buffer, pH 7) containing the purified GpUGT23 (30 μg), a ginsenoside compound (5 mM) and UDP-glucose (50 mM). For this assay, 4 different types of ginsenosides, including CK (Compound K), F2, Rd, and F1, were used and reacted with the enzyme of the present invention.

The reaction mixture was incubated at 37° C. for 12 hours, and then the products were analyzed by thin-layer chromatography (TLC) or high performance liquid chromatography (HPLC).

TLC analysis was performed using a mobile phase (acetone:methanol:DDW=65:35:10 vol/vol) and a 60F$_{254}$ silica gel plate (Merck, Germany). The resolved product on the TLC plate was detected by spraying the plate with 10% (vol/vol) sulfuric acid ($H_2SO_4$) and heating it at 110° C. for 5 minutes (FIG. 2).

HPLC analysis was performed using ODS(2) C18 column (Phenomenex, USA). Water and acetonitrile gradient application time and a component ratio are as follows: at a flow rate of 1 mL per minute, at 0 minutes, 68% water and 32% acetonitrile; 8 minutes, 35% water and 65% acetonitrile; 12 minutes, 0% water and 100% acetonitrile; 20 minutes, 0% water and 100% acetonitrile; 20.1 minutes, 68% water and 32% acetonitrile; and 28 minutes, 68% water and 32% acetonitrile (FIGS. 3 and 4).

Ginsenosides were detected by using a UV-detector (Agilent, USA) at a wavelength of 203 nm.

Experimental Example 1: Test of Glycosyltransfer Activity of GpUGT23 Specific to Glucose Linked by Glycosidic Bond at C-20 Position of PPD-Type or PPT-Type Ginsenoside Substrate specificity and regioselectivity of GpUGT23 were examined by the method described in Example 2.

First, the recombinant GpUGT of Example 1, GpUGT23, was reacted with 9 types of ginsenosides (PPD, $Rh_2$, $Rg_3$, CK, F2, Rd, PPT, F1, and $Rh_1$) in the presence of UDP-glucose, and the reaction products of CK, F2, Rd, and F1 were analyzed by TLC (thin-layer chromatography).

To further analyze these, 4 different types of ginsenosides (CK, F2, Rd, and F1) were incubated with GpUGT23, and then the products converted by the recombinant GpUGT23 were analyzed by TLC, and the results are shown in FIG. 2. The results were confirmed by comparing their migrating spots with migrating spots of CK, Gyp75 (gypenoside LXXV), F2, Gyp17 (gypenoside XVII), Rd, $Rb_1$, and F1 used as reference samples.

As a result, GpUGT23 converted CK, F2, Rd, and F1 into gypenoside LXXV, gypenoside XVII, $Rb_1$, and notoginsenoside U, respectively (FIG. 2).

Further, the present invention performed HPLC to further confirm the result of TLC, and the results are shown in FIGS. 3 and 4.

As a result, consistent with the TLC result, GpUGT23 did not react with PPD, $Rh_2$, $Rg_3$, PPT, and $Rh_1$ (FIGS. 3*a*-3*e*), but converted CK, F2, Rd, and F1 into gypenoside LXXV, gypenoside XVII, $Rb_1$, and notoginsenoside U, respectively (FIGS. 4*a*-4*e*).

These results suggest that GpUGT23 is an enzyme having UDP-glucose transfer activity for glucose linked by a glycosidic bond at the C-20 position of a PPD-type or PPT-type ginsenoside.

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds, are therefore intended to be embraced by the claims.

EFFECT OF THE INVENTION

UDP-glycosyltransferase of the present invention is a protein having glycosyltransfer activity for glucose linked by a glycosidic bond at the C-20 position of a PPD-type or PPT-type ginsenoside, and thus it can be used to produce a large amount of particular ginsenosides having two or more sugars at the C-20 position, such as gypenoside LXXV, gypenoside XVII, $Rb_1$, and notoginsenoside U.

What is claimed is:

1. A method of preparing a glycosylated protopanaxadiol (PPD)-type ginsenoside or a glycosylated protopanaxatriol (PPT)-type ginsenoside from a PPD-type ginsenoside or a PPT-type ginsenoside, wherein the glycosylated PPT-type ginsenoside and the PPD-type ginsenoside have a glucose that is linked by a glyosidic bond at the C-20 position, the method comprising:
   contacting the PPD-type ginsenoside or the PPT-type ginsenoside and UDP-glucose with:
   (i) an isolated Uridine diphosphate (UDP)-glycosyltransferase protein comprising an amino acid sequence that is at least 95% identical to the sequence of SEQ ID NO: 1, and which has activity for transferring a glucose moiety of UDP-glucose to the C-20 position of the PPD-type ginsenoside or the PPT-type ginsenoside, or
   (ii) an isolated host cell transformed with an expression vector, wherein the expression vector comprises a polynucleotide encoding a UDP-glycosyltransferase protein comprising an amino acid sequence that is at least 95% identical to the sequence of SEQ ID NO: 1, and which has glycosyltransfer activity for transferring a glucose moiety of UDP-glucose to the C-20 position of the PPD-type ginsenoside or the PPT-type ginsenoside or
   (iii) a culture comprising the host cell of (ii),
   to thereby prepare the glycosylated PPD-type ginsenoside or the glycosylated PPT-type ginsenoside.

2. The method of claim 1, wherein the PPD-type ginsenoside or the PPT-type ginsenoside is selected from the group consisting of compound K (CK), F2, Rd, F1, $Rg_1$ and Re.

3. The method of claim 2, wherein the UDP-glycosyltransferase protein catalyzes the conversion of CK into gypenoside LXXV, the conversion of F2 into gypenoside XVII, the conversion of Rd into $Rb_1$, the conversion of F1 into notoginsenoside U, the conversion of $Rg_1$ into notoginsenoside R3, and/or the conversion of Re into gluco-Re.

4. The method of claim 1, wherein the PPD-type ginsenoside and the PPT-type ginsenoside are chemically synthesized, or contained in an extract of ginseng or red ginseng.

5. The method of claim 1, wherein the UDP-glycosyltransferase protein comprises the amino acid sequence of SEQ ID NO: 1.

6. The method of claim 5, wherein the PPD-type ginsenoside or the PPT-type ginsenoside is selected from the group consisting of CK, F2, Rd, F1, $Rg_1$ and Re.

7. The method of claim 5, wherein the UDP-glycosyltransferase protein catalyzes the glycosylation of CK into gypenoside LXXV, the glycosylation of F2 into gypenoside XVII, the glycosylation of Rd into $Rb_1$, the glycosylation of F1 into notoginsenoside U, the glycosylation of $Rg_1$ into notoginsenoside R3, and/or the glycosylation of Re into gluco-Re.

8. The method of claim 5, wherein the PPD-type ginsenoside and the PPT-type ginsenoside are chemically synthesized, or contained in an extract of ginseng or red ginseng.

9. An expression vector comprising a polynucleotide encoding a UDP-glycosyltransferase protein and a heterologous promoter operably linked to the polynucleotide, wherein the UDP-glycosyltransferase protein comprises an amino acid sequence that is at least 95% identical to the sequence of SEQ ID NO: 1, and which has glycosyltransfer activity for transferring a glucose moiety of UDP-glucose to the C-20 position of a PPD-type ginsenoside or a PPT-type ginsenoside.

10. An isolated host cell transformed with the expression vector of claim 9.

11. The method of claim 1, wherein the isolated UDP-glycosyltransferase protein has been purified by affinity chromatography.

12. The method of claim 5, wherein the isolated UDP-glycosyltransferase protein has been purified by affinity chromatography.

* * * * *